(12) United States Patent
Ueda

(10) Patent No.: US 9,147,918 B2
(45) Date of Patent: Sep. 29, 2015

(54) EFFECTIVE RECOVERY OF LITHIUM FROM LITHIUM ION BATTERY WASTE

(75) Inventor: Masahiro Ueda, Kyoto (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 737 days.

(21) Appl. No.: 13/264,981

(22) PCT Filed: May 27, 2011

(86) PCT No.: PCT/US2011/038448
§ 371 (c)(1),
(2), (4) Date: Oct. 17, 2011

(87) PCT Pub. No.: WO2012/166104
PCT Pub. Date: Dec. 6, 2012

(65) Prior Publication Data
US 2012/0302779 A1  Nov. 29, 2012

(51) Int. Cl.
| | | |
|---|---|---|
| *C07F 7/12* | (2006.01) | |
| *H01M 10/54* | (2006.01) | |
| *C22B 26/12* | (2006.01) | |
| *C08G 77/06* | (2006.01) | |
| *C07F 7/21* | (2006.01) | |
| *H01M 10/0525* | (2010.01) | |

(52) U.S. Cl.
CPC ............... *H01M 10/54* (2013.01); *C07F 7/12* (2013.01); *C07F 7/21* (2013.01); *C08G 77/06* (2013.01); *C22B 26/12* (2013.01); *H01M 10/0525* (2013.01); *Y02E 60/122* (2013.01); *Y02W 30/84* (2015.05)

(58) Field of Classification Search
CPC ............ C07F 7/12; C07F 7/21; C08G 77/06; C22B 26/12
USPC ................ 556/406, 450, 460; 423/179.5, 181
See application file for complete search history.

(56) References Cited

U.S. PATENT DOCUMENTS

| | | | |
|---|---|---|---|
| 3,156,668 | A | 11/1964 | Pike |
| 4,370,237 | A | 1/1983 | Dain et al. |
| 7,695,625 | B2 | 4/2010 | Lyyra et al. |
| 8,124,283 | B2 | 2/2012 | Kang et al. |
| 2006/0083992 | A1 | 4/2006 | Nakanishi et al. |
| 2007/0059597 | A1 | 3/2007 | Nakanishi et al. |
| 2007/0224509 | A1 | 9/2007 | Aramata et al. |
| 2008/0171267 | A1 | 7/2008 | Kang et al. |
| 2010/0015514 | A1 | 1/2010 | Miyagi et al. |

FOREIGN PATENT DOCUMENTS

| | | |
|---|---|---|
| CN | 100441261 C | 12/2008 |
| GB | 1256704 A | 12/1971 |
| GB | 1265001 A | 3/1972 |
| JP | 01-160820 A | 6/1989 |
| JP | H10287864 A | 10/1998 |
| JP | 2001-023704 A | 1/2001 |
| JP | 2007-122885 A | 5/2007 |
| JP | 2007-194208 A | 8/2007 |
| JP | 2008-534493 A | 8/2008 |
| JP | 2010040458 A | 2/2010 |
| JP | 2010-277868 A | 9/2010 |
| WO | 2006/101328 A1 | 9/2006 |

OTHER PUBLICATIONS

"Cyclic Dimethylsiloxanes as Pseudo Crown Ethers: Syntheses and Characterization of Li(Me2SiO)5[Al{OC(CF3)3}4], Li(Me2SiO)6[Al{OC(CF3)3}4], and Li(Me2SiO)6[Al(OC(CF3)2Ph}4]**" Decken, Andreas and Wang, Xinping. Angewandte Chemie Int. Ed. 2006, 45.

Andreas Decken, Jack Passmore, Xinping Wang; Cyclic Dimethylsiloxanes as Pseudo Crown Ethers: Syntheses and Characterization of Li(Me2SiO)5[Al{O(CF3)3}4], Li(Me2SiO)6[Al{O(CF3)3}4], and Li(Me2SiO)6[Al{O(CF3)2Ph}4]; Angew. Chem. Int. Ed. 2006, 45, 2773-2777.

Nan et al.,"Recovery of metal values from a mixture of spent lithium-ion batteries and nickel-metal hydride batteries", Hydrometallurgy, vol. 84, No. 1-2, Oct. 2006, pp. 75-80.

Supplementary European Search Report dated Oct. 24, 2014 as received in Application No. 11 86 6884.

Wang et al.,"A novel recovery process of metal values from the cathode active materials of the lithium-ion secondary batteries", Hydrometallurgy, vol. 99, No. 3-4, Nov. 2009, pp. 194-201.

Xu et al.,"A review of processes and technologies for the recycling of lithium-ion secondary batteries", Journal of Power Sources, vol. 177, No. 2, Mar. 1, 2008, pp. 512-527.

Decken et al., Cyclic Dimethylsiloxanes as Psuedo Crown Ethers: Synthesis and Characterization of Li(Me2)SiO)5[Al{OC{CF3}3}4], Li(Me2)SiO)6[Al{OC(CF3)3}4], and Li(Me2)SiO)6[Al{OC(CF3)2Ph}4], Angew. Chem. Int. Ed., Germany, Wiley-VHC verlag GmbH & Co., 2006, vol. 45, pp. 2773-2777.

International Search Report and Written Opinion for International Patent Application No. PCT/US2011/038448 mailed Aug. 17, 2011.

Spiegel, E.F, et al., "Solvation of lithium salts within single-phase dimethyl siloxane bisphenoi-A carbonate block copolymer," Polymer, vol. 41, Issue 9, pp. 3365-3369 (Apr. 2000).

(Continued)

*Primary Examiner* — Sudhakar Katakam
(74) *Attorney, Agent, or Firm* — Maschoff Brennan

(57) ABSTRACT

A process for recovering Li-ions can include: providing a composition having Li-ions to be extracted therefrom; removing materials from the Li-ions; introducing one or more cyclic siloxane to the Li-ions so as to form one or more cyclic siloxane-Li-ion complexes; extracting the one or more cyclic siloxane-Li-ion complexes by one or more liquid-liquid extraction steps; separating an organic phase having the cyclic siloxane-Li-ion complexes from an aqueous phase; removing water from the organic phase; filtering the organic phase to obtain a filtrate; and obtaining one or more Li-ions (e.g., Li salts) from the filtrate.

19 Claims, 9 Drawing Sheets

(56) References Cited

OTHER PUBLICATIONS

Lee, W.S, "Anion receptor based on cyclic siloxanes substituted with trifluoromethanesulfonylamide for solid polymer electrolytes," Macromolecular Research, vol. 18, No. 3, pp. 266-270 (2007).
International Preliminary Report on Patentability for International Application No. PCT/US2011/038448 issued on Dec. 2, 2013.
Decken et al., "Cyclic Dimethylsiloxanes as Pseudo Crown Ethers: Syntheses and Characterization of Li(Me2SiO)5[Al{OC(CF3)3}4], Li(Me2SiO)6[Al{OC(CF3)3}4], and Li(Me2SiO)6[Al(OC(CF3)2Ph}4]†", Angewandte Chemie International Edition, vol. 45, Issue 17, Apr. 21, 2006, pp. 2773-2777.
Toxco Inc., 125 East Commercial Street, Suite A, Anaheim, CA 92801; http://www.toxco.com/processes.html, retrieved Nov. 26, 2010.

EFFECTIVE RECOVERY OF LITHIUM FROM LITHIUM ION BATTERY WASTE

CROSS-REFERENCE TO RELATED APPLICATIONS

The present application is a U.S. national stage filing under 35 U.S.C. §371 of International Application No. PCT/US2011/038448, filed on May 27, 2011.

BACKGROUND

Unless otherwise indicated herein, the materials described in this section are not prior art to the claims in this application and are not admitted to be prior art by inclusion in this section.

Lithium ion (Li-ion) batteries have become prevalent as a portable power source for portable electronic devices. As technology advances toward wireless devices, the need for Li-ion batteries will continue to increase. Additionally, the automotive industry is in the process of developing vehicles that use significantly more Li-ion batteries for power than ever before. As such, the use of Li-ion batteries is predicted to continue to increase into the foreseeable future.

While the use of Li-ion batteries can be helpful in many instances, all Li-ion batteries eventually lose the ability to provide adequate power and to be replaced with a fresh battery. When a Li-ion battery is dead, there are disposal concerns due to the number of heavy metals and toxic chemicals that are present. Many of the materials used in Li-ion batteries have some value that can be obtained if the material can be recycled.

Lithium (Li), in the form of Li-ions, is an example of a material that is a prime candidate for recycling from spent batteries. Currently, the techniques for recycling Li-ions are limited, and recycling Li-ions is not as prevalent as for other metals. However, with the predicted increase in Li-ion battery usage, improvements in Li-ion recycling continue to be sought.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

Figure 1A:
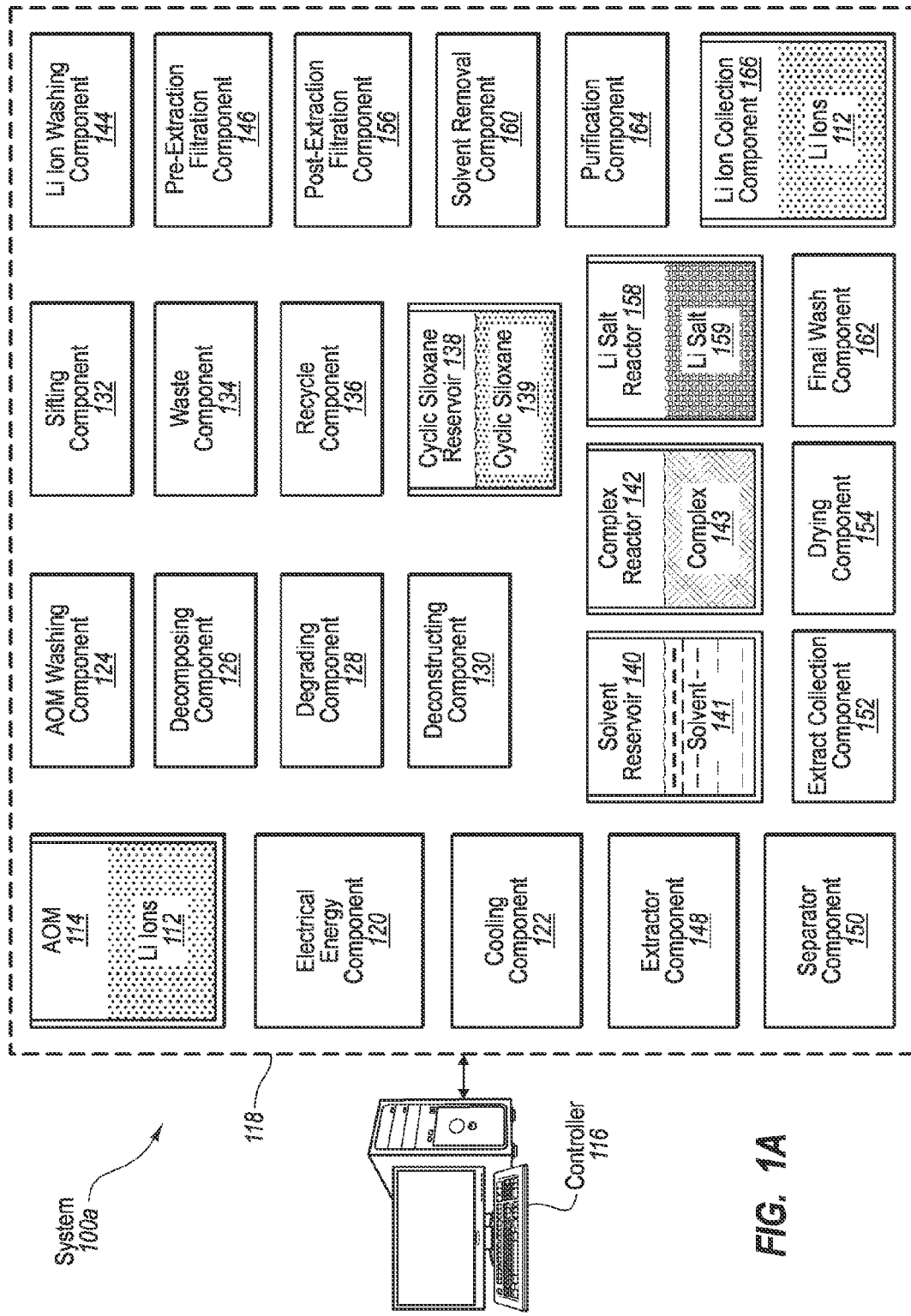
FIGS. 1A-1B are schematic diagrams of embodiments of Li recovery systems.

arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that various aspects of the present disclosure, as generally described herein, and illustrated in the figures, can be arranged, substituted, combined, separated, and designed in a wide variety of different configurations, all of which are explicitly contemplated herein.

This disclosure is generally drawn, inter alia, to methods, apparatus, systems, devices and compositions related to recovery of Li-ions.

Generally, Li-ions can be recovered from an article of manufacture (AOM). The recovered Li-ions can be obtained in a sufficient purity for use in substantially any manner, such as being recycled into additional Li-ion batteries. In some examples, a process for recovering Li-ions can include extracting one or more Li-ion with one or more cyclic siloxanes from an AOM facture. The Li-ion extraction process can be performed by liquid-liquid extraction in a suitable extraction system by forming a complex between the cyclic siloxanes and the Li-ions. The Li-ions to be recovered can be provided in an AOM that is decomposed, degraded, and/or deconstructed into a crude Li-ion composition. Otherwise, a crude Li-ion composition can be provided pre-processed for Li extraction. Additional pre-processing may be useful if the quality of the crude Li-ions is unsatisfactory. A Li-ion battery, such as a secondary cell, is an example of an AOM.

In some embodiments, a process for recovering Li-ions can include one or more operations such as: providing a composition (e.g., composition from AOM) having Li-ions to be extracted therefrom; removing materials from the Li-ions such as by removing materials from an AOM or composition having the Li-ions; introducing one or more cyclic siloxane to the Li-ions so as to form one or more cyclic siloxane-Li-ion complexes; extracting the one or more cyclic siloxane-Li-ion complexes by one or more liquid-liquid extraction steps; separating an organic phase having the cyclic siloxane-Li-ion complexes from an aqueous phase; removing water from the organic phase; filtering the organic phase to obtain a filtrate; and obtaining one or more Li-ions (e.g., Li salts) from the filtrate.

In some embodiments, a Li-ion recovery composition can include one or more crude Li-ions and one or more cyclic siloxanes. The crude Li-ions can be obtained from an AOM in sufficient condition for liquid-liquid extraction. The crude Li-ions may also be included in a suitable solvent, such as dichloromethane.

In some embodiments, a Li-ion recovery system can include a first composition having crude Li-ions and a second composition having a cyclic siloxane. Each composition can be included in a separate container or vessel. Additionally, each composition may include a suitable solvent, such as dichloromethane.

Embodiments disclosed herein may relate to compositions, systems, and processes useful in the recovery of Li-ions from article of manufacture (AOM). The compositions can be configured to be suitable for use in liquid-liquid extraction with highly hydrophobic cyclic siloxane functioning as a ligand for Li-ions, where the cyclic siloxanes can sequester Li-ions through interaction with the ring oxygen atoms. Cyclic siloxanes have an excellent ability to selectively capture Li-ions, as described in more detail below. Briefly, the cyclic siloxanes can efficiently recover Li-ions from waste Li-ion cells. The Li-ion recovery process using cyclic siloxanes may provide an improvement over recovery using amphiphilic crown ethers, which are inefficient.

Cyclic siloxanes can form strong complexes with Li-ions with high selectivity. The cyclic siloxanes are selective for Li-ions, even though the equilibrium constant of the complex-forming reaction is moderate ("Cyclic Dimethylsiloxanes as Pseudo Crown Ethers: Synthesis and Characterization of $Li(Me_2SiO)_5[Al\{OC(CF_3)_3\}_4]$, $Li(Me_2)SiO)_6[Al\{OC(CF_3)_3\}_4]$, and $Li(Me_2)SiO)_6[Al\{OC(CF_3)_2Ph\}_4]$"); A Decken et al.; *Angew. Chem. Int. Ed.* (2006) 45, 2773-2777, which is hereby incorporated by reference in its entirety). Also, cyclic siloxanes are highly hydrophobic and can be effective in extracting Li into organic solvents. In contrast, crown ethers may dissolve in both water and organic solvents, and thereby may not be as efficient in liquid-liquid extractions. The hydrophobic property of cyclic siloxane has been found to be advantageous for a process involving liquid-liquid extraction of Li-ions from waste such as Li-ion batters, as described in detail below.

The Li-ions can be provided in an AOM or a discrete composition obtained from an AOM, where the AOM material may be processed so that Li can be recovered and recycled. After the Li-ions are removed, the AOM or materials therefrom can be disposed of or recycled. The discrete composition can be processed to provide a crude Li-ion composition suitable for liquid-liquid extraction with cyclic siloxanes. In some instances crude Li-ion compositions may be conditioned to be suitable for liquid-liquid extraction through multiple pre-processes, as described in detail below.

The crude Li-ion compositions can be washed with water to extract water-soluble materials, including Li-ions. The water used for washing the crude Li-ion composition can be subjected to filtration in order to remove residues from the Li-ions. The aqueous filtrate includes the Li-ions. The aqueous filtrate can be mixed with some amount of an organic solvent (e.g., toluene) having some amount of cyclic siloxanes. The relative amounts of organic solvent and cyclic siloxanes compared to the amount of crude Li-ion composition can vary depending on the quality of the crude Li-ion composition as well as the concentration of Li-ions available for extraction. Mechanical agitation and bubble generation can be used to facilitate increased water/organic solvent interfacial surface areas in order to promote interaction with cyclic siloxanes and Li-ions. The cyclic siloxanes may selectively form complexes with the Li-ions and partition into the organic phase through liquid-liquid extraction. After sufficient separation of the water and organic solvent, the organic solvent can be collected and the Li-ions can be obtained. The final recovery efficiency of Li-ions may increase as the concentration of cyclic siloxane increases in the liquid-liquid extraction composition, and thereby the liquid-liquid extraction can use cyclic siloxane itself as the organic phase. However, when cyclic siloxane is used as the organic solvent, the composition may have higher viscosity, and the extraction system can be modified to handle viscous liquids. Otherwise, some other organic solvent can be used in an amount sufficient to lower the viscosity into a workable range.

In some embodiments, the liquid-liquid extraction process can be repeated several times with the crude Li-ion composition. Each liquid-liquid extraction process can use fresh cyclic siloxanes, or cyclic siloxanes recovered from the extracted Li-ions from subsequent processing. The liquid-liquid extraction can be repeated on the crude Li-ion composition until substantially all of the Li-ions are removed, or such that the remaining material can be recycled or sent to waste. However, any level of Li extraction can be beneficial, such as up to or about 10% Li-ion extraction, up to or about 25% Li-ion extraction, up to or about 50% Li-ion extraction, up to or about 75% Li-ion extraction, up to or about 80% Li-ion extraction, up to or about 90% Li-ion extraction, up to or about 95% Li-ion extraction, or up to or about 99% Li-ion extraction.

Surprisingly and unexpectedly, cyclic siloxanes can be used to extract Li-ions more effectively than crown ethers. If Li-ion extraction is conducted using a crown ether instead of cyclic siloxane, the amphiphilic nature of the crown ether may result in substantially equal distribution between the aqueous phase and the organic phase. As such, the Li-ions may not be effectively transferred to the organic phase. Furthermore, if a crown ether having a high interfacial activity is used, the crown ether may not partition into either the aqueous phase or the organic phase; however, such a crown ether can partition between the aqueous and organic phases to form a tri-phase composition or a suspension, which may be difficult to separate. Cyclic siloxanes may be considered superior to crown ethers in conducting liquid-liquid extraction due to the favorable binding between the cyclic siloxanes and the Li-ions as well as the high degree of partitioning of the cyclic siloxane-Li-ion complexes into the organic phase.

The organic phase obtained from each liquid-liquid extraction can be separated from the water phase. The separation can be performed by allowing the aqueous and organic phases to separate in a separation vessel, and then selectively drawing the organic phase from the aqueous phase, or vice versa. The separated organic phase can then be collected for further processing.

The organic phase can be processed to remove residual water left from the liquid-liquid extraction. There are various processes that be used to remove water from an organic composition, and thereby dry the organic composition. As used herein, "drying" may include processes that remove water from the cyclic siloxane-Li complexes, such as by removing residual water from the organic phase having the cyclic siloxane-Li-ion complexes. Examples of drying the collected organic phase can include using a water-absorbing medium to absorb water from the organic phase or using evaporation to remove the water. In a particular example, the organic phase can be dried by being combined with magnesium sulfate particles so that water can partition out of the organic phase and into the magnesium sulfate particles. Other solid particulates that selectively absorb water over organic solvents can be used in anhydrous formats. Such anhydrous solid particulates can be sufficiently porous or have interstitial space for absorbing and retaining water. The hydrated solid particulates can then be removed from the organic phase by separating the liquid organic phase from the solid particulates, or vice versa. In one example, the solid particulates can be removed by filtration, and the organic filtrate having the cyclic siloxane-Li complexes is substantially devoid of water. While solid particulates can be used to absorb water, larger solid materials can be used; however, a higher surface area may promote higher water absorption.

After the organic solvent having the cyclic siloxane-Li complexes has been filtered to remove solids, the organic solvent can be removed to leave a Li-ion residue. The resulting Li-ion residue can be a Li salt, such as a cyclic siloxane-Li salt. The organic solvent of the filtrate can be removed by standard organic solvent practices, such as by using heat to increase the solvent temperature by several tens of degrees Celsius above room temperature or ambient conditions. The organic solvent removal process can also be conducted under reduced pressures that are lower than standard atmospheric pressures at the location at which the process is performed. For example, standard rotary evaporation can be used to remove the organic solvent.

When a cyclic siloxane, such as 2,2,4,4,6,6,8,8,10,10-decamethylcyclopentasiloxane (i.e., $Si_5O_5$ cyclic siloxane; cyclopentamethicone), is used as the organic solvent, the cyclic siloxane-Li complex can be broken down so that the cyclic siloxane can be removed. Energy provided into the system for heat can break apart the complex. The energy can be provided sufficiently to increase the temperature of the cyclic siloxane past its boiling point, which is 90° C. at 10 mmHg.

The resulting Li residue that is obtained after removal of the organic solvent can be washed with a washing solvent. The washing solvent can be the same solvent that was removed, or it can be a different organic solvent. An example of a suitable solvent includes toluene or others described below. The washing with an organic solvent process can be followed by another solvent removal process. The washing with an organic solvent can lead to the Li-ions being disassociated from the cyclic siloxane, and the hydrophobic nature and boiling point of the cyclic siloxane can result in its removal along with the organic solvent. The result of washing with organic solvent can result in pure Li-ions, such as in the form of Li-ion salts. A counter ion for the Li-ions can be introduced with the organic solvent during the washing process, such as a carbonate counter ion to produce a Li carbonate salt that can be used in Li-ion batteries.

The Li-ion recovery process described herein is highly selective, and uses significantly less energy than distillation. Also, the Li-ions can be provided in the organic solvent so that the solvent removal and/or washing processes can be omitted for further energy savings. Since the Li recovery process described herein is highly selective, steps that consume a large amount of energy, such as distillation and solvent removal, may not be necessary and can be omitted. Therefore, the Li-ion recovery process may be advantageous in terms of cost as well as Li-ion recovery performance.

However, when is it desired to have Li-ions that are highly purified, for example, further processing may need to be performed. Such processing may include distillation.

FIG. 1A is a schematic diagram of an embodiment of a Li recovery system 100a that is arranged in accordance with at least some examples described herein. As illustrated, a system 100a can be configured for extracting Li-ions 112 from a device 114. The device 114 can be any article of manufacture (AOM), such as but not limited to the examples of devices 114 having Li-ions 112 described herein. The system 100a may include a controller 116 that is operably coupled to a network 118 shown by the dashed line box. The controller 116 can include the features of a computing system as described in more detail in connection with FIG. 3. The network 118 is illustrated by the dashed line box to represent that components in the network 118 are operably coupled such that each component can transmit and/or receive data over the network 118. Networks 118 are well known, and can include wired, optical, and wireless network technologies. As such, each component can be outfitted with hardware (not shown) and/or software configured for data communications over the network 118. Non-limiting examples of hardware can include a transceiver and associated electronic and/or optical components configured for data communications. The controller 116 can include hardware and/or software configured to provide instructions over the network 118 to each component of the system 100a, and also to receive data from the individual components.

The system 100a in FIG. 1A can include one or more of the following components (which are described in detail below): electrical energy component 120; cooling component 122; washing component 124; decomposing component 126; degrading component 128; deconstructing component 130; sifting component 132; waste component 134; recycle component 136; cyclic siloxane reservoir 138 having cyclic siloxane 139; solvent reservoir 140 having solvent 141; complex reactor 142 having cyclic siloxane-lithium ion complexes 143; lithium ion washing component 144; pre-extraction filtration component 146; extractor component 148; separator component 150; collection component 152; drying component 154; post-extraction filtration component 156; Li salt reactor 158 having Li salt 159; solvent removal component 160; final washing component 162; purification component 164; and Li-ion collection component 166 having Li-ion 112 product. These components can be arranged in any manner that is suitable for recovering Li-ions from an AOM 114 or composition having the Li-ions 112. The dashed box can indicate that the components can be operably coupled so that a process product obtained from one component can be transferred to another component. The operable couplings can include liquid conduits, conveyor belts, land vehicles, and/or any other appropriately configured machinery. Also, the dashed box can also indicate that the individual components are operably coupled with the network 118, controller 116, and with any of each other in order to perform Li-ion 112 recovery.

Generally, the electrical energy component 120 can be capable of removing residual electrical energy from the Li-ions 112 or composition having the Li-ions 112. The electrical energy component 120 can include an electronic ground feature or a circuit having an electronic ground feature that grounds the Li-ions 112 so that the electrical energy is discharged therefrom. An electrically conductive line can be provided to the Li-ions 112 of composition thereof so that the electrical energy can be dissipated.

The cooling component 122 can be capable of reducing the temperature of the AOM 114 and lithium ions 112 to less than room temperature or ambient conditions. Cooling components 122 are well known and can include various features that allow for implementing a cooling process to lower reactivity of the Li-ions 112. While heat sinks can be used for drawing heat energy from the Li-ions 112, some heat sinks may not be sufficient for reducing the temperature of the Li-ions 112 so that they are less reactive. As such, the cooling component 122 can be configured to actively cool the Li-ions 112. Active cooling can be achieved by including a refrigeration unit with the cooling component 122. The refrigeration unit can provide the refrigeration and cooling of the Li-ions 112. A standard freezer can be used as a cooling component 122. Active cooling can also be achieved by introducing the Li-ions 112 to a cooling composition, such as liquid nitrogen. The Li-ions 112 can be submerged in liquid nitrogen or operably associated with the liquid nitrogen so that the Li-ions 112 are sufficiently cooled. Other cooling compositions, such as dry ice-acetone baths, may also be used for active cooling of the Li-ions 112. The cooling component 122 can be used for reducing the temperature of the Li-ions 112 or composition thereof so that the Li-ions 112 can be less reactive and suitable for mechanical processing. The cooling component 122 can reduce the temperature of the Li-ions 112 from room temperature to less than or about 0° C. (32° F.), to less than or about −50° C. (−58° F.), to less than or about −100° C. (−148° F.), to less than or about −150° C. (−238° F.); to less than or about −198° C. (−325° F.), or to less than or about −200° C. (−328° F.). Thus, the cooling component 122 can be configured for reducing temperature of the Li-ions 112 below a threshold such that the lithium ion is not explosively reactive, and optionally so as to cause the Li-ions 112 to be substantially inert.

The washing component 124 can be any type of washing apparatus to clean the AOM 114 or otherwise remove contaminants from the AOM 114 and compositions having the Li-ions 112. While the washing component 124 can be useful for removing contaminants, care should be taken as the Li-ions 112 may also be washed away. As such, the compositions being washed usually are structurally sound and typically do not degrade or release the Li-ions 112 upon exposure to water and washing. Li-ion battery compositions can be washed without significant loss of Li-ions 112. The washing component 124 can be configured as any type of apparatus that uses water and optionally detergent for washing contaminants from the AOM 114. The features of dishwashers, clothes washers, industrial washers, or others can be implemented in the washing component 124.

The decomposing unit 126 can process the AOM 114 or discrete composition having the Li-ions 112 so as to separate or resolve a composition having the Li-ions 112 into constituent parts or elements. The decomposing unit 126 can use various processes in order to decompose the AOM 114 and/or composition having the Li-ions 112. The decomposing unit 126 can be a bioreactor that uses bacteria to decompose the AOM 114 into its solid and liquid elements. The decomposition unit 126 can be configured to retain the AOM 114 or composition having the Li-ions 112 so that natural or natural-mimetic processes can break down the composition into a crude Li-ion composition. The decomposing component 126 can include a cooling unit that operates as the cooling component 122 in order to maintain the Li-ions 112 below a threshold temperature.

The degrading component 128 can use chemicals and chemical processes to degrade the AOM 114 or composition having the Li-ions 112 into a crude Li-ion composition. The chemicals and chemical processes can be selected based on the composition having the Li-ions 112. The chemicals can include various solvents that can dissolve the composition in order to liberate the Li-ions 112. The chemical processes can include heating, cooling, or pressure changes that can degrade the composition having the Li-ions 112 or cause chemicals in contact with the composition to be more effective at liberating Li-ions 112. The degrading component 128 can include a cooling unit that operates as the cooling component 122 in order to maintain the Li-ions 112 below a threshold temperature.

The deconstructing component 130 can use physical or mechanical processes in order to deconstruct or break apart the AOM 114 and compositions having the Li-ions 112. The physical or mechanical processes can involve the use of machinery having features that can break apart, cut, shear, shred, grind, mill, compact, crush, or otherwise devolve the AOM 114 into small pieces or particles that can be subsequently processed into a crude Li-ion composition. The deconstructing component 130 can include a cooling unit that operates as the cooling component 122 in order to maintain the Li-ions 112 below a threshold temperature.

The sifting component 132 can sift the products of the washing component 124, decomposing component 126, degrading component 128, deconstructing component 130 so as to remove large particles or solids from smaller particles or solids. The particles or solids having the Li-ions 112 can then be processed for recovery of the Li-ions 112. The sifting component 132 can include one or more sieves that can sift through the materials of the AOM 114, and select particles having Li-ions 112 based on size. Also, the sifting component 132 can include a magnetic unit that can be used to remove magnetically responsive materials from the Li-ions 112, which are not magnetically responsive.

The waste component 134 can receive waste materials of the AOM 114 removed from Li-ions 112. The waste component 134 can be any type of receptacle for waste management and removal.

The recycle component 136 can receive and recycle waste materials of the AOM 114 removed from lithium ions 112. The recycle component 136 can be similar to the waste component 134, except that the destination of the material is for recycling as opposed to being discarded as waste. The recycling component 136 can be any type of recyclable material repository.

In some embodiments, a Li-ion recovery system can exclude one or more of the following pre-extraction processes: electrical energy component 120; cooling component 122; washing component 124; decomposing component 126; degrading component 128; deconstructing component 130; sifting component 132; waste component 134; and recycle component 136. These individual or combined components can be considered to be pre-processing components that pre-process the AOM 114 and Li-ions 112 prior to extraction and recovery as described herein.

The system 100b in FIG. 1B can include one or more of the following components (which are described in detail below): cyclic siloxane reservoir 138 having cyclic siloxane 139; solvent reservoir 140 having solvent 141; complex reactor 142 having cyclic siloxane-lithium ion complexes 143; lithium ion washing component 144; pre-extraction filtration component 146; extractor component 148; separator component 150; collection component 152; drying component 154; post-extraction filtration component 156; Li salt reactor 158 having Li salt 159; solvent removal component 160; final washing component 162; and Li-ion collection component 166 having Li-ion 112 product. The dashed box can indicate that the components can be operably coupled so that a process product obtained from one component can be transferred to another component. The operable couplings can include liquid conduits, conveyor belts, land vehicles, and any other appropriately configured machinery. Also, the dashed box can also indicate that the individual components are operably coupled with the network 118, controller 116, and with any of each other in order to perform Li-ion 112 recovery.

The cyclic siloxane reservoir 138 can contain cyclic siloxanes 139 with or without a solvent 141. The cyclic siloxane reservoir 138 can be any type of container or vessel, such as those that are used in chemical processing systems. The cyclic siloxane reservoir 138 can include one type of cyclic siloxane 139 or a mixture of two or more different types of cyclic siloxanes 139. The cyclic siloxane reservoir 138 can include discrete compartments that contain different cyclic siloxanes 139.

The solvent reservoir 140 can contain a solvent 141 for Li-ions 112 and/or cyclic siloxane-Li-ion complexes 143. The solvent reservoir 140, and any other reservoir described herein, can be similar to the cyclic siloxane reservoir 138. The solvent reservoir 140 can include a single type of solvent 141, such as dichloromethane, or a combination of miscible solvents 141, such as dichloromethane and cyclic siloxanes 139. The solvent reservoir 140 can have multiple discrete compartments that can each include different solvents 141.

The complex reactor 142 can retain the Li-ions 112 and cyclic siloxanes 139 during the formation of the cyclic siloxane-Li complexes 143. The complex reactor 142 can be any standard chemical reactor vessel. The complex reactor 142 can include any components sufficient for facilitation of cyclic siloxane-Li complex 143 formation, such as temperature control units (e.g., heaters) and pressure control units that can modulate the temperature and pressure to values sufficient for formation of the complex 143. Also, the complex reactor 142 can be configured to provide for introducing a crude or washed composition having Li-ions 112 into a solution having one or more cyclic siloxanes 139. The complex reactor 142 can also be configured to allow the one or more cyclic siloxanes 139 to bind with the Li-ions 112 to form a cyclic siloxane-lithium ion complex 143.

The Li-ion washing component 144 can wash the Li-ions 112 before being processed through the complex reactor 142, and/or for washing the cyclic siloxane-Li complexes 143 after being processed through the complex reactor 142. Usually, the Li-ion washing component 144 is configured for washing the crude Li-ion composition prior to being introduced into the complex reactor 142 so that any undesirable residues can be washed from the Li-ions 112. The washing component 144 can be configured as any standard washer that uses water to wash an item or composition. The washing component 144 can include a water inlet and components for mechanical agitation and/or bubble generation. The washing component 144 can include a pressure unit so that pressure within the washing component 144 can be modulated to induce bubble generation. Agitation can be important in order to loosen and remove residues from the Li-ions 112. The washing component 144 can use water for washing, but may also be adapted to use organic solvents for washing. In some examples, the washing solvent is a solvent for Li-ions 112, such as water.

The filtration component 146 can filter the Li-ions 112 contained within the washing medium. Usually, the washing medium is water which contains the Li-ions 112, and the filter filters substances and residues that are not water soluble or less water soluble. The filtration component 146 can allow for the passage of Li-ions 112 into the filtrate. The filtration component 146 can include one or more filters arranged in a manner that allows for filtration of residues from the washing medium (e.g., water) having Li-ions 112. Also, the filtration component 146 can filter the cyclic siloxane-Li complexes 143. In any event, the filtrate obtained from the filtration component 146 can be collected for extraction.

The extractor component 148 can facilitate extraction of cyclic siloxane-Li complexes 143 from a reaction medium. The extractor component 148 can be configured for liquid-liquid extraction, and can include mechanical components useful for facilitating extraction, such as mechanical agitator to sufficiently mix the aqueous and organic phases. The aqueous phase can arise from the washing medium or it can be introduced into the extractor component 148 after formation of the complexes 143 in the complex reactor 142. The organic phase can arise from the solvent reservoir 140 as the solvent 141. Also, the organic phase can be the solvent 141 used in the complex reactor 142 to facilitate formation of the complexes 143. The extractor component 148 can include any units that are capable of performing bubble generation, temperature change, pressure change, or any other process that facilitates extraction of cyclic siloxane-Li complexes 143 from water.

Additionally, the extractor component 148 can include features for preparing a liquid-liquid extraction composition having water and an organic solvent 141. The extractor component 148 can also include features for preparing the liquid-liquid extraction composition to have the Li-ions 112 to be extracted. The Li-ions 112 to be extracted can be in the complex 143 with the cyclic siloxanes 139. As such, the extraction composition can be prepared to include the cyclic siloxanes 139. In some examples, a liquid-liquid extraction composition includes the cyclic siloxanes 139 as an organic phase. In some examples, the liquid-liquid extraction composition can include toluene as the organic phase. Also, the extractor component 148 can be configured for performing multiple liquid-liquid extractions in order to remove Li-ions 112 from an aqueous phase.

The separator component 150 can separate the aqueous phase from the organic phase after extraction of the cyclic siloxane-Li complexes 143 into the organic phase within the extractor component 148. The separator component 150 may be independent or part of the extractor component 148. The separator component 150 can function like a separation funnel in order to remove one liquid phase (organic phase) from another immiscible liquid phase (aqueous phase). The organic phase includes the cyclic siloxane-Li complexes 143, which preferentially partition into an organic phase over an aqueous phase. The separator component 150 can provide the aqueous phase back to the extractor component 148 so that additional extraction processes can be performed to remove any cyclic-siloxane-Li complexes 143 that remain in the aqueous phase.

The collection component 152 can collect the organic phase having the cyclic siloxane-Li-ion complexes 143 obtained from the separator component 150. The collection component 152 can be any storage vessel or container, which can be fluidly coupled to the separator component 150.

The drying component 154 can remove water from the cyclic-siloxane-Li complexes 143 or from extracted Li-ions 112 or extracted Li salts. The drying component 154 can include any features that may promote the removal of any residual water from the organic phase having the cyclic siloxane-Li complexes 143. The removal of water can be facilitated by evaporation or absorption into a hygroscopic medium or particulate. For example, the organic phase can be heated to a temperature that evolves water into water vapor, which can be vented from the drying component 154. Alternatively, the drying component 154 can include magnesium sulfate particles or other hygroscopic substances that can absorb water therein.

The post-extraction filtration component 156 can remove any solid matter that may be present with the Li-ions 112. For example, when the drying component 154 uses a hygroscopic solid to absorb water from the organic phase, the hygroscopic solid can be removed from the organic phase along with entrapped water by filtration. The post-extraction filtration component 156 can include one or more filters that can collect solids and allow the passage of the organic phase as the filtrate. The filtrate can be collected as it has soluble Li-ions 112 and/or cyclic siloxane-Li complexes 143. The filtrate can be a final product.

The Li salt reactor 158 can convert the Li-ions 112 into a salt product other than the cyclic siloxane salt. The Li salt reactor 158 can include various salts having counter ions that can associate with Li-ions 112 to form Li salts 159. A primary example includes carbonate salts so that Li carbonate can be formed, as Li carbonate is used in Li-ion batteries. The Li salt 159 can be a final product.

The solvent removal component 160 can remove the organic solvent 141 from the extracted cyclic siloxane-Li complexes 143. Solvent 141 removal can be facilitated in any manner that can remove an organic solvent from the cyclic siloxane-Li complexes 143. Examples include the use of heat and/or reduced pressure to remove the solvent 141. In some examples, the removal of solvent can be facilitated at a temperature above or about 0° C., above or about 10° C., above or about 20° C., above or about 30° C., above or about 40° C., above or about 50° C., above or about 60° C., above or about 70° C., above or about 80° C., above or about 90° C., above or about 100° C., above 200° C., or even greater. The temperature can be increased to above the boiling point of the solvent 141.

Also, the removal of the organic solvent can be conducted under reduced pressure, such as a reduced pressure is less than about 1 atm. A rotary evaporation unit can be used for the solvent removal component 160, and can operate under heat and/or reduced pressure. The removal of solvent 141 can be conducted to a degree that also disassociates the complexes 143 so that the cyclic siloxane 139 can also be removed from the Li-ions 112.

In some embodiments, the Li-ion recovery system 100b can include a purification component 164 that can provide the Li-ions 112 at high purity. For example, the purification component 164 can be a distillation column that can distil substances away from the Li-ions 112 to provide purified lithium ions (e.g., Li-ion salts 159).

In some embodiments, the purification component 164 can purify the Li-ions by electrolysis. Electrolysis can be used to separate the positive and negative charges, and thereby the positive Li-ions 112 can be separated from negatively charged counter ions. The positive Li-ions 112 can then be collected in high purity.

The final washing component 162 can wash the extracted Li-ions 112 to further remove any additional contaminants and to increase the purity. The final washing component 162 can use a solvent 141, such as toluene or water. The final washing component 162 can be operably coupled to the solvent removal component 160 so that the solvent 141 used in the final washing component 162 can be removed. After removal of the solvent, consequently heating the residue including namely Li-ion and cyclic siloxane complex, and evaporating the ligand, cyclic siloxane allows Li salts to be left as a product. When it is hard to separate Li-ion salt from the cyclic siloxane, burning the ligand at around 400° C. or higher temperature can be effective in removing other substances in order to obtain pure Li ion salt. In some examples, the washing composition can include salts to displace the cyclic siloxanes. In some examples, the washing composition can exclude cyclic siloxanes. The Li-ion collection component 166 can be a reservoir that collects the purified Li-ions 112 or Li salts 159. The Li-ion collection component 166 can be any type of vessel or container capable of retaining the Li-ions 112.

FIGS. 2A-2D are block diagrams of embodiments of Li-ion recovery processes 200a arranged in accordance with at least one of the embodiments described herein. The Li-ion recovery process 200a can be used with the systems of FIGS. 1A-1B or any other system capable of recovering Li-ions with cyclic siloxanes. The components in FIG. 1A correspond to the individual process steps shown in FIG. 2A.

Figure 2A:
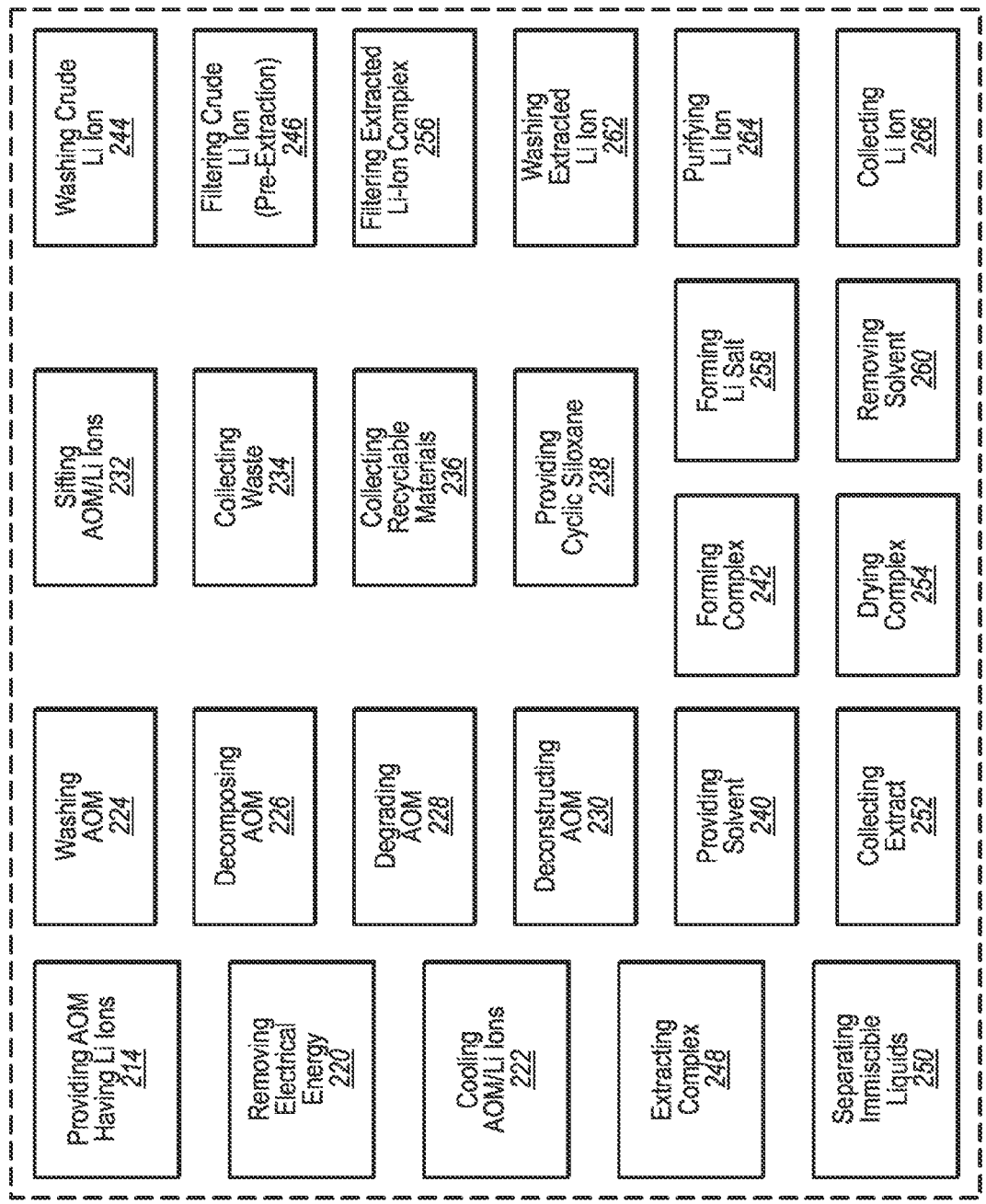
FIGS. 2A-2D are block diagrams of embodiments of Li recovery processes.

The Li-ion recovery process 200a in FIG. 2A can include one or more of the following processes, operations, functions, and/or steps: providing article of manufacture (AOM) having Li-ions (block 214); removing electrical energy (block 220); cooling AOM/Li-ions (block 222); washing AOM (block 224); decomposing AOM (block 226); degrading AOM (block 228); deconstructing AOM (block 230); sifting AOM/Li-ions (block 232); collecting waste (block 234); collecting recyclable materials (block 236); providing cyclic siloxane (block 238); providing solvent (block 240); forming complex (block 242); washing crude Li-ion (block 244); filtering crude Li-ion (pre-extraction) (block 246); extracting complex (block 248); separating immiscible liquids (block 250); collecting extract (block 252); drying complex (block 254); filtering extracted Li-ion complex (block 256); forming Li salt (block 258); removing solvent (block 260); washing extracted Li-ion (block 262); purifying Li-ion (block 264); and collecting Li-ion (block 266). These individual process steps can be conducted in any suitable order in order to extract Li-ions with cyclic siloxanes. As such, the dashed box indicates that the individual processes can be performed in substantially any order that provides extracted Li-ions. Also, one or more of the individual processes of FIG. 2A can be omitted or combined.

In some embodiments, the processes of FIG. 2A can be performed with components of FIG. 1A as follows: the electrical energy component 120 can be used for removing electrical energy from the Li-ions 112 prior to extraction (block 222); the cooling component 122 can be used for cooling AOM/Li-ions before or during pre-extraction processing (block 222); the AOM washing component 124 can be used for washing the AOM before extraction to remove contaminants (block 224); the decomposing component 126 can be used for decomposing the AOM into a crude Li-ion composition (block 226); the degrading component 128 can be used for degrading the AOM into a crude Li-ion composition (block 228); the deconstructing component 130 can be used for deconstructing the AOM into particles suitable for use in extraction (block 230); the sifting component 132 can be used for sifting AOM/Li-ions in order to remove material from the Li-ions 112 (block 232); the waste component 134 can be used for collecting waste generated from pre-extraction processing (block 234); the recycle component 136 can be used for collecting recyclable materials (block 236); the cyclic siloxane reservoir 138 can be used for providing cyclic siloxane 139 to the Li-ions 112 for complex formation (block 238); the solvent reservoir 140 can be used for providing solvent 141 to the complex reactor 142 as well as to any component that uses a solvent 141 as described (block 240); the complex reactor 142 can be used for forming complexes 143 between the Li-ions 112 and the cyclic siloxanes 139 (block 242); the Li-ion washing component 144 can be used for washing crude Li-ions 112 or washing the complexes 143 (block 244); the pre-extraction filtration component 146 can be used for filtering crude Li-ions 112 (block 246); the extractor component 148 can be used for extracting complexes 143 from an aqueous phase by liquid-liquid extraction (block 248); the separator component 150 can be used for separating immiscible liquids so that the organic phase having the complexes 143 can be separated from the aqueous phase (block 250); the extract collection component 152 can be used for collecting the organic phase extract (block 252); the drying component 154 can be used for drying the complexes 143 to remove water (block 254); the post-extraction filtration component 156 can be used for filtering the extracted complexes 143 (block 256); the Li salt reactor 158 can be used for forming Li salts 159 from the complexes 143 (block 258); the solvent removal component 160 can be used for removing solvent 141 from the Li-ions 112 (block 260); the final wash component 162 can be used for washing the extracted Li-ions 112 (block 262); the purification component 164 can be used for purifying the Li-ions 112 (block 264); and the Li-ion collection component can be used for collecting the Li-ions 112 (block 266).

Figure 2B:
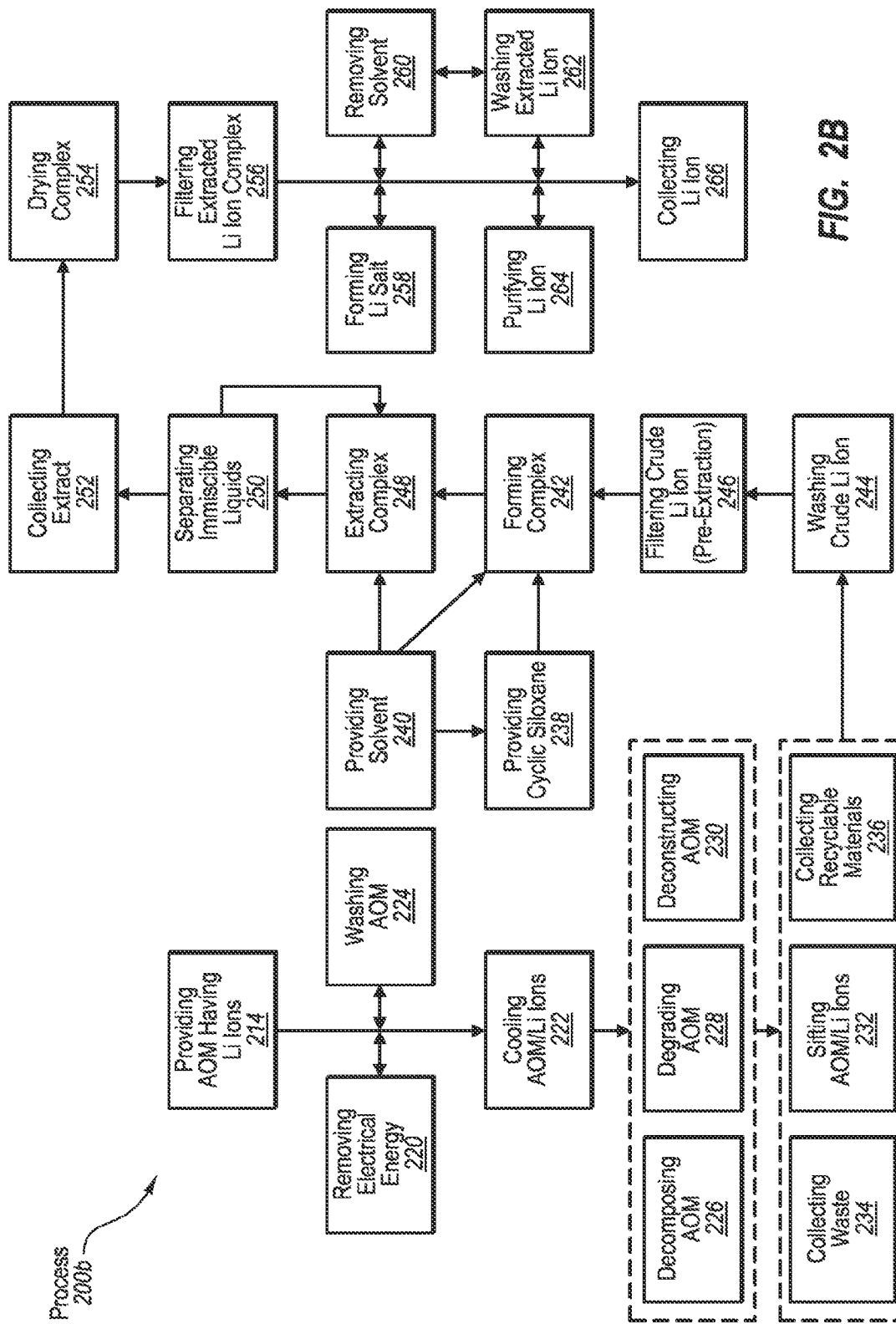

The Li-ion recovery process 200b in FIG. 2B is shown as a flow diagram that illustrates the relationship between the individual processes of FIG. 2A. The Li-ion recovery process 200b can include the following processes, operations, functions and/or steps: providing AOM having Li-ions (block 214) can be an initial process; removing electrical energy (block 220) can optionally be conducted on the provided AOM or discrete material of the AOM that includes the Li-ions; cooling AOM/Li-ions (block 222) can be conducted before any optional physical destruction of the AOM; washing AOM (block 224) can optionally be conducted before physical destruction of the AOM; decomposing AOM (block 226) can optionally be performed in order to provide a crude Li-ion composition for extraction; degrading AOM (block 228) can optionally be conducted in order to provide a crude Li-ion composition for extraction; deconstructing AOM (block 230) can optionally be conducted in order to provide a crude Li-ion composition; sifting AOM/Li-ions (block 232) can optionally be conducted to remove large particles or solids to form a crude Li-ion composition for extraction; collecting waste (block 234) can be conducted after any pre-extraction processing in order to discard waste materials from the AOM; collecting recyclable materials (block 236) can be conducted after any pre-extraction processing in order to recycle any recyclable materials from the AOM; providing cyclic siloxane (block 238) can be conducted in order to provide a sequestration agent for Li-ions for forming complexes; providing solvent (block 240) can optionally be conducted in order to provide a solvent for the cyclic siloxanes and complexes formed with the Li-ions; forming complex (block 242) can be done in order to provide an extractable complex that preferentially partitions into an organic phase for liquid-liquid extraction, and can be done after any of the foregoing processes; washing crude Li-ion (block 244) can be conducted prior to or after formation of the complexes in order to remove residues from the Li-ions and after any of the pre-extraction processes; filtering crude Li-ion (pre-extraction) (block 246) can be conducted after the washing of the crude Li-ions in order to remove residues therefrom; extracting complex (block 248) can be conducted after formation of the complexes; separating immiscible liquids (block 250) can be conducted after the complex is extracted into the organic phase; collecting extract (block 252) can be conducted after the organic phase is separated from the aqueous phase; drying complex (block 254) can be conducted after the organic phase having the complexes has been collected after separation from the aqueous phase; filtering extracted Li-ion complex (block 256) can be conducted after drying the separated organic phase in order to remove any water-absorbing particles or solids; forming Li salt (block 258) can be conducted in order to change the Li-ion counter ion from a cyclic siloxane to any other counter ion, such as a carbonate counter ion; removing solvent (block 260) can be conducted to remove the organic solvent from the Li-ions after drying and filtering the complex; washing extracted Li-ion (block 262) can be conducted to further purify the Li-ions, and may be conducted in association to the removing solvent (block 260); purifying Li-ion (block 264) can be conducted in order to increase Li-ion purity, such as by distillation; and collecting Li-ion (block 266) can be conducted at any point in the process 200b when the Li-ions are sufficient for a product. For example, the process 200b can be conducted substantially as shown by the flow diagram. In the flow diagram, the dashed boxes indicate alternate processes that can be performed individually, sequentially, or in combination. Double-sided arrows indicate optional processes that can be conducted at various intervals within the process 200b.

Figure 2C:
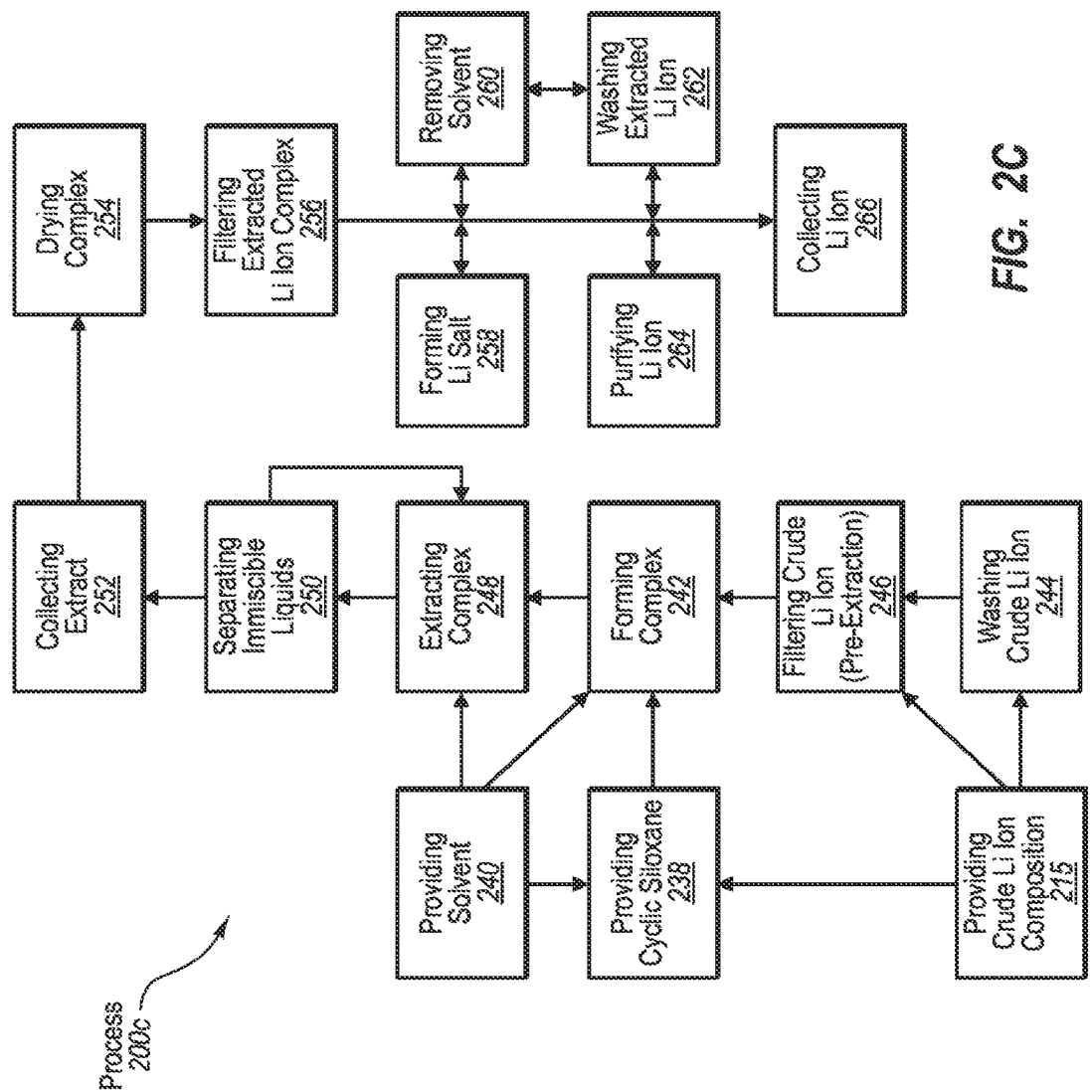

The Li-ion recovery process 200c in FIG. 2C is shown to include the following processes, operations, functions, and/or steps: providing crude Li-ion composition 215; providing cyclic siloxane 238; providing solvent 240; washing crude Li-ion 244; filtering crude Li-ion (pre-extraction) 246; forming complex 242; extracting complex 248; separating immiscible liquids 250; collecting extract 252; drying complex 254; filtering extracted Li-ion complex 256; forming Li salt 258; removing solvent 260; washing extracted Li-ion 262; purifying Li-ion 264; and collecting Li-ion 266. In this process 200c, the pre-extraction processing steps have been omitted as the Li-ions are provided in a crude Li-ion composition that is sufficient for extraction after optionally washing (block 224) and filtering (block 246) the crude Li-ion composition. Any of these processes can be performed with the components as described in connection to FIGS. 1A and 2A. The sequence of processes can be substantially as illustrated in the flow diagram, where the arrows indicate the sequence of processes.

Additionally, FIG. 2C shows that the Li-ion recovery process 200c has various alternatives after providing the crude Li-ion composition (block 215). For example, after being provided, the crude Li-ion composition can be washed with water (block 244), and then followed by filtering crude Li-ion before extraction (block 246). In another alternative, the washing process (block 244) can be omitted if the crude Li-ion composition is sufficient for filtering or if it is provided in an aqueous composition. In yet another alternative, the crude Li-ion composition can be combined with the cyclic siloxane (block 238) with or without solvent in order to form the complexes (block 242). Also, the solvent can be provided at one or more of the various intervals that are shown (block 240). However, the cyclic siloxane can be provided as the lone solvent.

Figure 2D:
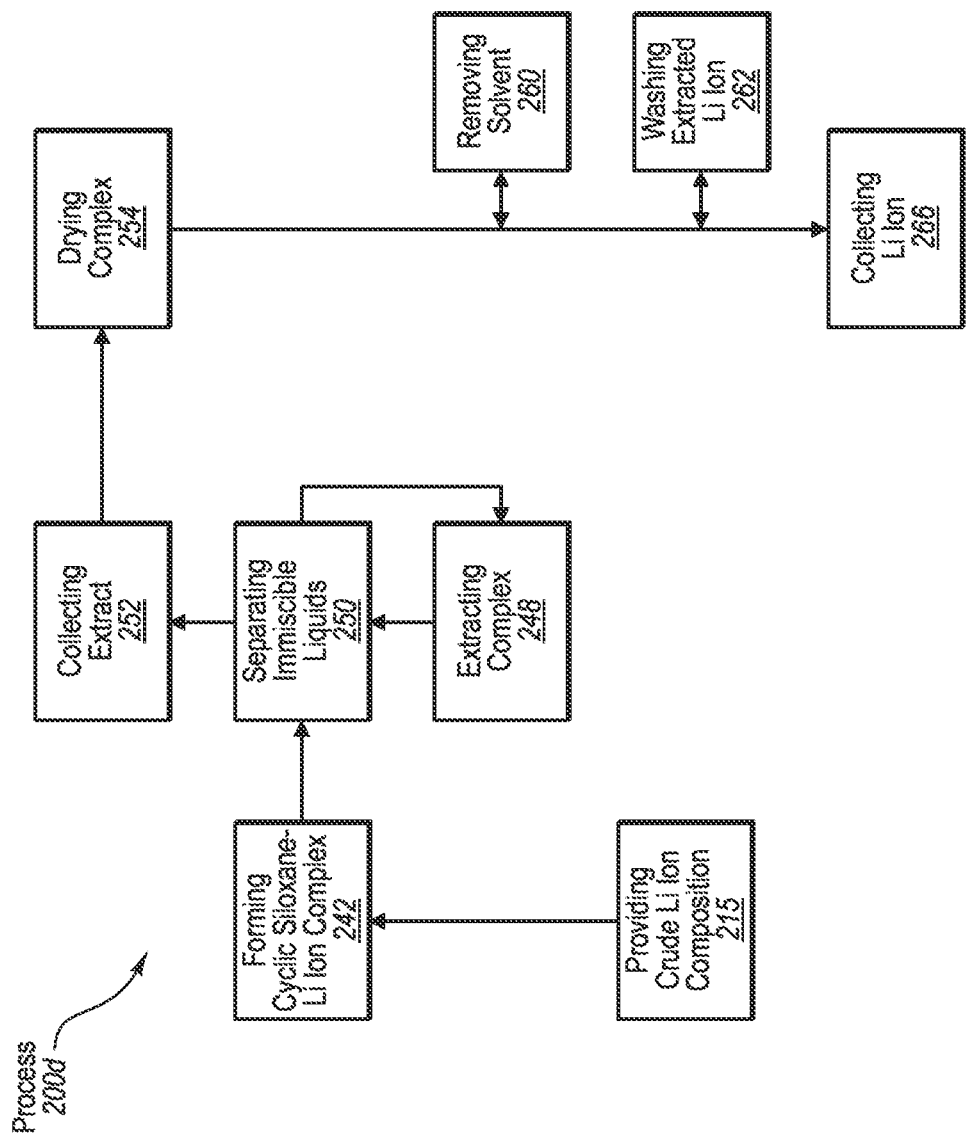

The Li-ion recovery process 200d in FIG. 2D is shown to include the following processes, operations, functions, and/or steps: providing crude Li-ion composition (block 215); forming complex (block 242); extracting complex (block 248); separating immiscible liquids (block 250), where the aqueous phase undergo additional extraction (block 248); collecting extract (block 252); drying complex (block 254); (optionally) washing extracted Li-ion (block 262); (optionally) purifying Li-ion (block 264); and collecting Li-ion for use as a product (block 266). This Li-ion extraction process 200d can be suitable in many instances to provide a useful Li-ion product.

In some embodiments, method for recovering lithium ions are described that may include: providing a composition having lithium ions to be extracted therefrom; removing materials from the lithium ions; introducing one or more cyclic siloxane to the lithium ions so as to form one or more cyclic siloxane-lithium ion complexes; extracting the one or more cyclic siloxane-lithium ion complexes by one or more liquid-liquid extraction steps; separating an organic phase having the cyclic siloxane-lithium ion complexes from an aqueous phase; removing water from the organic phase; filtering the organic phase to obtain a filtrate; and obtaining one or more lithium ions from the filtrate. In one example, the composition is an article of manufacture. In another example, the composition includes raw ore. In another example, the composition is derived from an article of manufacture. For example, the composition can be from a Li-ion battery.

In some aspects, removing of materials from the lithium ions may include removing materials from an article of manufacture having the Li-ions. In another aspect, the removing the materials from the lithium ions includes removing materials from a composition having the Li-ions. Prior to extraction, the method can include removing various materials from the lithium ion to be extracted, such as non-lithium metals, polymers, ceramics, or combinations thereof.

In some embodiments, systems for recovering lithium ions from a composition are described that can include one or more of the following: a controller configured to facilitate the system for recovering lithium ions from the composition; a cyclic siloxane reservoir including one or more cyclic siloxanes contained therein; a complex reactor that is operably coupled to the cyclic siloxane reservoir so as to receive one or more cyclic siloxanes therefrom and that is operably coupled to the controller so as to be capable receiving instructions therefrom, wherein the complex reactor is adapted to form cyclic siloxane-lithium ion complexes; and an extractor component operably coupled to the complex reactor so as to be capable of receiving the cyclic siloxane lithium ion complexes therefrom and operably coupled to the controller so as to be capable of receiving instructions therefrom, wherein the extractor component is adapted to extract cyclic siloxane-lithium ions. Any of the other components that are described herein can also be included in the system, and may be operably coupled with the controller as well as with each other to facilitate Li-ion recovery. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various examples. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or processing systems, which can, of course, vary. It is also to be understood that the terminology used herein is for the purpose of describing particular embodiments only, and is not intended to be limiting.

In an illustrative embodiment, any of the operations, processes, methods, or other events described herein can be implemented as computer-readable instructions stored on a computer-readable medium. The computer-readable instructions can be executed by a processor of a computer, mobile unit, a network element, and/or any other computing device.

There is little distinction left between hardware and software implementations of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices, systems, and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that various embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 1B:
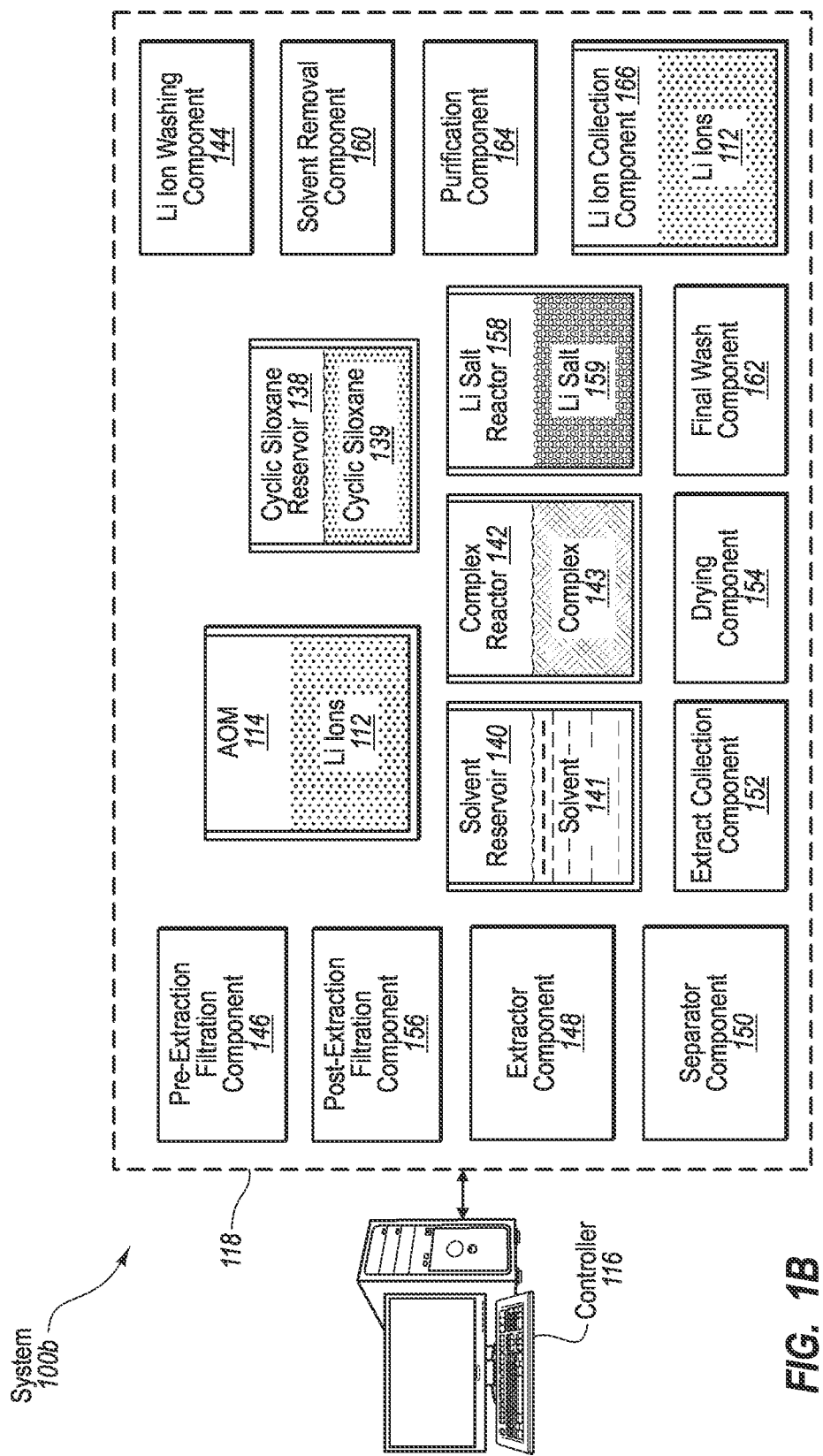

FIGS. 1A-1B illustrate a system (generally 100) that have individual components operably coupled together in a network as shown by the dashed box 118. The network 118 and the individual components thereof controlled by the controller 116. The dashed box also indicates that the individual components can be operably coupled so that the material processed in one component can be transported to any other appropriate component. For example, tubing can be connected between the various components so that liquid or flowable material can be passed therebetween, such as between the extractor component 148 and separator component 150. In another example, a conveyor belt or other means of propulsion of solid materials can be used to operably couple the electrical energy component 120 with the cooling component 122. The possible number of operable couplings is significant, and is more easily represented by the dashed box that identifies that any of the components may be operably coupled, such as by some physical, electronic, or wireless coupling.

Figure 3:
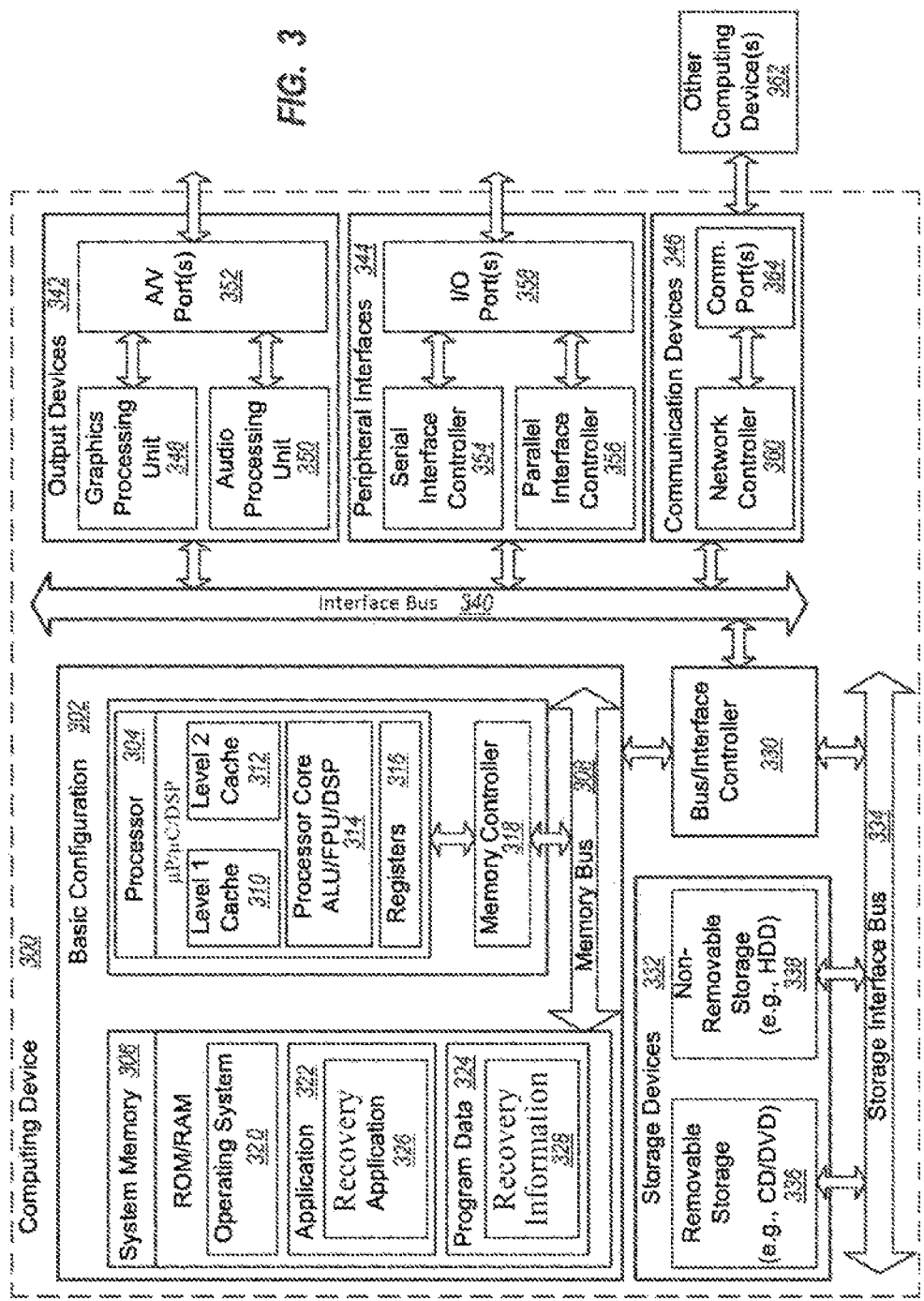
FIG. 3 is a schematic diagram of an embodiment of a computing device.

FIG. 3 is a schematic diagram of an embodiment of a computing device 300 that is arranged in accordance with at least one of the embodiments described herein for operating with the systems described herein, such as illustrated in FIGS. 1A-1B, for any of the processes for recovering Li-ions from an article of manufacture or a crude Li-ion composition. The computing device 300 can be arranged with or operably coupled with any of the components, network, and/or system in accordance with at least some embodiments described herein. In a very basic configuration 302, computing device 300 generally includes one or more processors 304 and a system memory 306. A memory bus 308 may be used for communicating between processor 304 and system memory 306.

Depending on the desired configuration, processor 304 may be of any type including but not limited to a microprocessor (µP), a microcontroller C), a digital signal processor (DSP), or any combination thereof. Processor 304 may include one more levels of caching, such as a level one cache 310 and a level two cache 312, a processor core 314, and registers 316. An example processor core 314 may include an arithmetic logic unit (ALU), a floating point unit (FPU), a digital signal processing core (DSP Core), or any combination thereof. An example memory controller 318 may also be used with processor 304, or in some implementations memory controller 318 may be an internal part of processor 304.

Depending on the desired configuration, system memory 306 may be of any type including but not limited to volatile memory (such as RAM), non-volatile memory (such as ROM, flash memory, etc.) or any combination thereof. System memory 306 may include an operating system 320, one or more applications 322 (e.g., software program), and program data 324. Application 322 may include a Li-ion recovery application 326 that is arranged to perform the functions as described herein including those described with respect to processes 200a-200d of FIGS. 2A-2D. Program Data 324 may include Li-ion recovery information 328 that may be useful for analyzing the purity of the Li-ions provided by an analytical unit of the purification component 164. In some embodiments, application 322 may be arranged to operate with program data 324 on operating system 320. This described basic configuration 302 is illustrated in FIG. 3 by those components within the inner dashed line.

Computing device 300 may have additional features or functionality, and additional interfaces to facilitate communications between basic configuration 302 and any required devices and interfaces. For example, a bus/interface controller 330 may be used to facilitate communications between basic configuration 302 and one or more data storage devices 332 via a storage interface bus 334. Data storage devices 332 may be removable storage devices 336, non-removable storage devices 338, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 306, removable storage devices 336 and non-removable storage devices 338 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 300. Any such computer storage media may be part of computing device 300.

Computing device 300 may also include an interface bus 340 for facilitating communication from various interface devices (e.g., output devices 342, peripheral interfaces 344, and communication devices 346) to basic configuration 302 via bus/interface controller 330. Example output devices 342 include a graphics processing unit 348 and an audio processing unit 350, which may be configured to communicate to various external devices such as a display or speakers via one or more A/V ports 352. Example peripheral interfaces 344 include a serial interface controller 354 or a parallel interface controller 356, which may be configured to communicate with external devices such as input devices (e.g., keyboard, mouse, pen, voice input device, touch input device, etc.) or other peripheral devices (e.g., printer, scanner, etc.) via one or more I/O ports 358. An example communication device 346 includes a network controller 360, which may be arranged to facilitate communications with one or more other computing devices 362 over a network communication link (i.e., network 118) via one or more communication ports 364.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 300 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 300 may also be implemented as a personal computer including both laptop computer and non-laptop computer configurations.

In some embodiments, a Li-ion recovery composition can include one or more crude lithium ions, and one or more cyclic siloxanes. The Li-ions of a crude Li-ion composition are considered to be crude Li-ions. The Li-ion recovery composition can have one or more materials from the AOM or discrete composition thereof from which the crude Li-ion composition was obtained. In some examples, the composition is devoid of amphiphilic crown-ethers. In some examples, the cyclic siloxane can include 3 or more Si atoms in a ring, 4 or more Si atoms in a ring, 5 or more Si atoms in a ring, 6 or more Si atoms in a ring, or 7 or more Si atoms in a ring. Theoretically, the ring may include up to about 40-45 Si atoms in the ring, where large rings of 10 or more Si atoms may complex with 2 or more Li-ions. An example of a cyclic siloxane can include from 5 to 7 Si atoms in a ring.

In some embodiments, the cyclic siloxane can include a cyclic alkylsiloxane. The cyclic alkylsiloxane can include one or more substituted or unsubstituted alkyl groups conjugated to the Si atoms. The substituted or unsubstituted alkyl groups can include two alkyl groups conjugated to each Si atom. In some examples, at least one of the two alkyl groups can include a dimethyl group or derivative thereof. A derivative of the methyl group can include one or more of the hydrogen atoms being substituted with a substituent, such as substituted or unsubstituted alkyl groups or other substituents described herein.

In some embodiments, the Li recovery composition can include an organic solvent. The organic solvent can include toluene, tetrachlorothylene, acetone, methyl acetate, ethyl acetate, hexane, petrol ether, citrus terpenes, alcohols, ethanol, pentanes, benzenes, dioxanes, chloroform, diethylether, tetrahydrofuran, dimethylformamide, acetonitrile, dimethyl sulfoxide, formic acid, butanol, isopropanol, methanol, or other suitable solvent or combinations thereof.

In some embodiments, the Li recovery composition can include water. The water may be in a roughly 1:1 ratio with organic solvent, or range from about 1:10 to 10:1.

The cyclic siloxanes can have various embodiments, and can include derivatives of the embodiments illustrated herein. Some examples include cyclic alkylsiloxanes, such as cyclic dimethylsiloxanes, which may be referred to as pseudo crown ethers. The cyclic dimethylsiloxane can be represented by $D_n$ (i.e., $D_n=(Me_2SiO)_n$, where n=1-45). As used herein, "Me" when used in connection with chemical names, formulas or structures is meant to refer to a methyl group, such as a terminal methyl (e.g., —$CH_3$) or a methylene (e.g., —$CH_2$—). Specific cyclic alkylsiloxane-Li complexes can include without limitation the following, $Li(Me_2SiO)_5[Al\{OC(CF_3)_3\}_4]$ (i.e., $LiD_5[Al_F]$), $Li(Me_2SiO)_6$, $Li(Me_2SiO)_6[Al\{OC(CF_3)_3\}_4]$ (i.e., $LiD_6[Al_F]$), $Li(Me_2SiO)_6[Al\{OC(CF_3)_2Ph\}_4]$ (i.e., $LiD_6[Al_{PhF}]$), or others. As used herein, "Ph" when used in connection with chemical names, formulas or structures is meant to refer to a phenyl group, such as a terminal phenyl group (e.g., $C_6H_5$) or a phenyl group within a chain (e.g., $C_6H_4$), and may be a substituted phenyl group (e.g., $C_6H_{6-n}R_n$) where R is any substituent including portions of molecular chains and n is 1, 2, 3, 4, 5, or 6. As used herein, "$[Al_F]$" is "$[Al\{OC(CF_3)_3\}_4]$." As used herein, "$[Al_{PhF}]$" is "$[Al\{OC(CF_3)_2Ph\}_4]$."

The cyclic siloxane-Li complex may also include a counter ion. The counter ion can be selected to modulate (e.g., increase or decrease) the binding potential between the cyclic siloxane and Li-ions. For example, the counter ion can be $Al\{OC(CF_3)_3\}_4$, $Al\{OC(CF_3)_2Ph\}_4$, carbonate, or other. The followings are examples of counter ions: inorganic anions, such as $Cl^-$, $Br^-$, $I^-$, $(SO_4)^{2-}$, $NO_3^-$ and $(PO_4)^{3-}$; and organic anions such as carboxylic anion.

The cyclic siloxane can form a complex with a Li-ion so as to form a cyclic siloxane-Li complex. Additional information regarding cyclic siloxane-Li complexes can be found in "Cyclic Dimethylsiloxanes as Pseudo Crown Ethers: Synthesis and Characterization of $Li(Me_2SiO)_5[Al\{OC(CF_3)_3\}_4]$, $Li(Me_2SiO)_6[Al\{OC(CF_3)_3\}_4]$, and $Li(Me_2SiO)_6[Al\{OC(CF_3)_2Ph\}_4]$"; A Decken et al.; *Angew. Chem. Int. Ed.* (2006) 45, 2773-2777, which is incorporated herein by specific reference.

Figure 4:
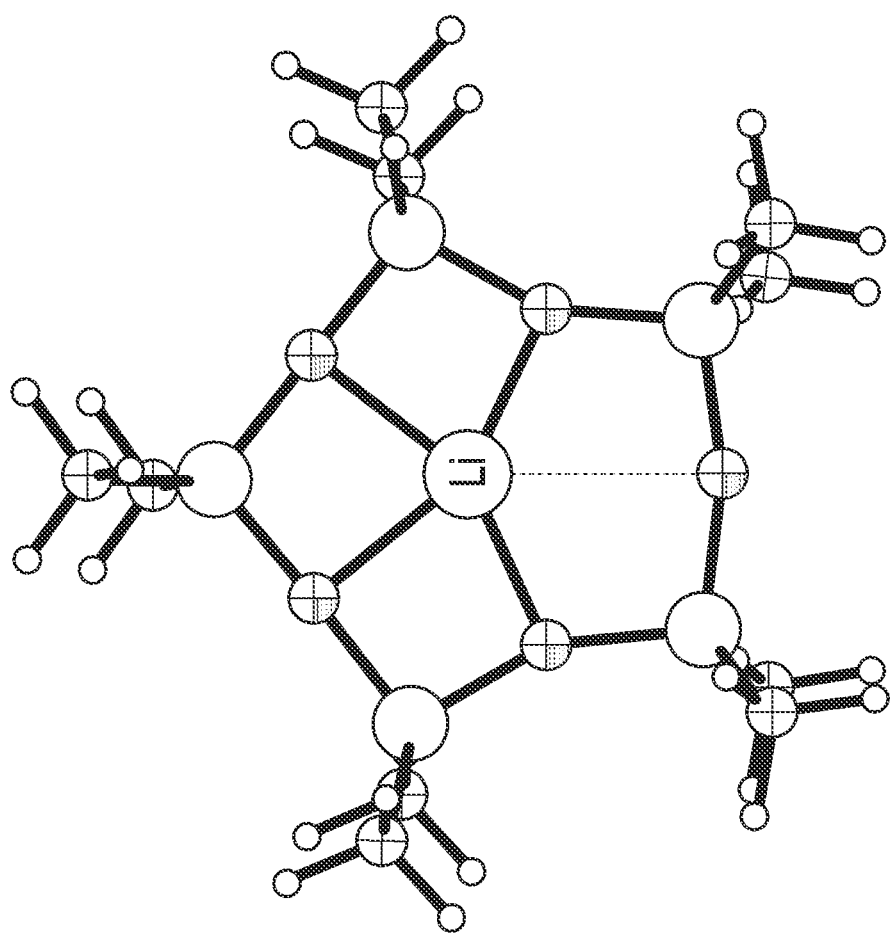
FIG. 4 is an illustration of a chemical structure of an embodiment of a cyclic $Si_5O_5$ siloxane-Li complex.

FIG. 4 is an illustration of a chemical structure of an embodiment of a cyclic $Si_5O_5$ siloxane-Li complex, $Li(Me_2SiO)_6$, where large open circles are Si, crossed circles with the lower left quadrant filled are O, open crossed circles are C, small open circles are H.

Figure 5:
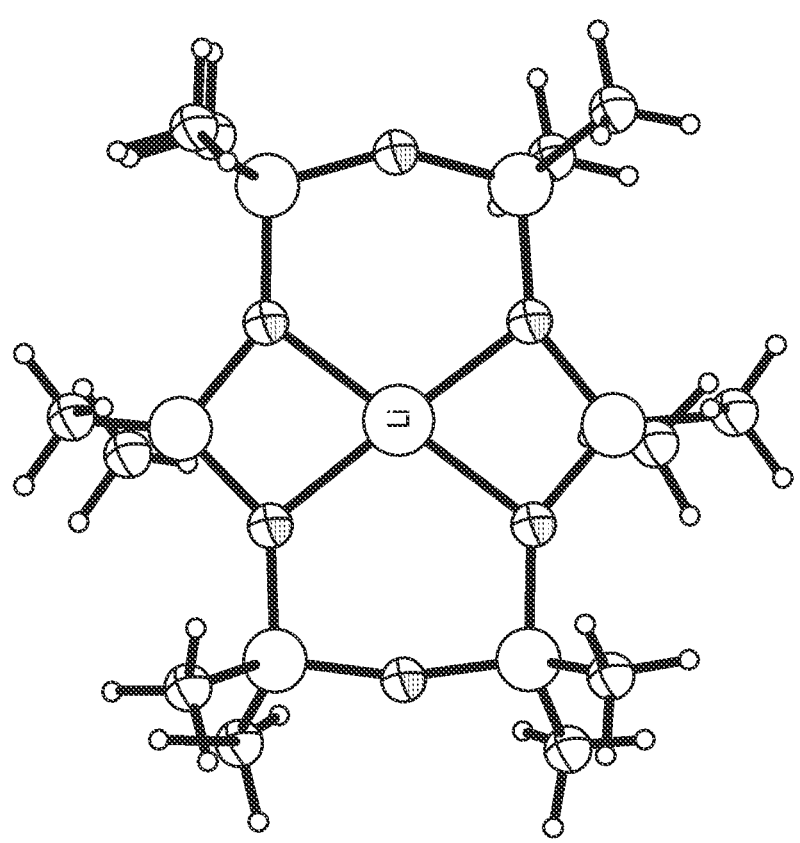
FIG. 5 is an illustration of a chemical structure of an embodiment of a cyclic $Si_6O_6$ siloxane-Li complex.

FIG. 5 is an illustration of a chemical structure of an embodiment of a cyclic $Si_6O_6$ siloxane-Li complex, $Li(Me_2SiO)_6$, where large open circles are Si, crossed circles with the lower left quadrant filled are O, open crossed circles are C, small open circles are H.

The cyclic siloxanes can be provided as derivatives of the embodiments described herein. As such, the cyclic siloxanes can include one or more hydrogen atoms being substituted with a substituent. The substituents can each be selected to include one or more of halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. Examples of the substituents can be selected from the group of $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbony (—(CO)—O-alkyl), $C_6$-$C_{20}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$≡$C^-$), isothiocyanato (—S—C≡N), azido (—N=$N^+$=$N^-$), formyl (—(CO)—H), thioformyl (—(CS)—H), amino (—$NH_2$), mono- and di-($C_1$-$C_{24}$ alkyl)- substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$S_2$—$O^-$)'$C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), phosphino (—$PH_2$), derivatives thereof, and combinations thereof.

The term "alkyl" or "aliphatic" as used herein refers to a substituent that includes a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a substituent having a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a substituent having a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein refers to a substituent having an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein refers to a substituent having an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to a substituent having an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to a substituent having an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to a substituent having univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

In some embodiments, a Li recovery system can include a first composition having crude lithium ions and a second composition having a cyclic siloxane. These are two separate compositions that can be included in separate containers. The cyclic siloxane can be any cyclic siloxane, such as those described herein.

In some embodiments, the Li recovery system is devoid of amphiphilic crown-ethers.

In some embodiments, the Li recovery system can include any of the components in FIG. 1A in any suitable arrangement for Li recovery with cyclic siloxanes.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various examples. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A method for recovering lithium ions, the method comprising:
    providing an article of manufacture having lithium ions;
    processing the article of manufacture to obtain a crude lithium-containing composition;
    introducing cyclic siloxanes to the crude lithium-containing composition so that the cyclic siloxane complexes with the lithium ions;
    preparing a liquid-liquid extraction composition having an organic solvent and water such that the complexes of the cyclic siloxanes and lithium ions partition into the organic solvent; and
    extracting the complexes of cyclic siloxanes and lithium ions by liquid-liquid extraction with an organic solvent and water.

2. The method of claim 1, further comprising removing a material of the article of manufacture from the lithium ions before introducing the cyclic siloxanes.

3. The method of claim 1, further comprising washing the lithium ions or a composition having lithium ions with water and detergent to remove substances of the article of manufacture before introducing the cyclic siloxanes.

4. The method of claim 1, further comprising removing residues from the lithium ions before introducing the cyclic siloxanes.

5. The method of claim 1, further comprising filtering a composition derived from the article of manufacture having the lithium ions before introducing the cyclic siloxanes.

6. The method of claim 1, further comprising collecting an organic phase having the complex of lithium ion and cyclic siloxane by separating the organic phase from a water phase.

7. The method of claim 6, further comprising removing water from the collected organic phase having the lithium ion and cyclic siloxane.

8. The method of claim 6, further comprising filtering the organic phase having the lithium ion and cyclic siloxane.

9. The method of claim 8, further comprising collecting a filtrate having the lithium ion from the filtration step.

10. The method of claim 6, after the liquid-liquid extraction, further comprising washing lithium ion with an organic solvent to obtain lithium ions.

11. The method of claim 1, further comprising purifying the lithium ions by removing the cyclic siloxane from the lithium ions.

12. The method of claim 1, comprising performing the recovery of lithium ions with a system, the system comprising:
    a controller configured to facilitate the system for recovering the lithium ions from the composition;
    a cyclic siloxane reservoir including one or more of the cyclic siloxanes contained therein;
    a complex reactor that is operably coupled to the cyclic siloxane reservoir so as to receive one or more cyclic siloxanes therefrom and that is operably coupled to the controller so as to be capable receiving instructions therefrom, wherein the complex reactor is adapted to form the cyclic siloxane-lithium ion complexes; and
    an extractor component operably coupled to the complex reactor so as to be capable of receiving the cyclic siloxane lithium ion complexes therefrom and operably coupled to the controller so as to be capable of receiving instructions therefrom, wherein the extractor component is adapted to extract the cyclic siloxane-lithium ion complexes with the liquid-liquid extraction composition.

13. The method of claim 12, the system further comprising one or more of the following:
    an electrical energy component operably coupled to the controller so as to be capable of receiving instructions therefrom and adapted to remove residual electrical energy from lithium ions in the composition;
    a cooling component operably coupled to the controller so as to be capable of receiving instructions therefrom and adapted to cool the lithium ions or composition having the lithium ions;
    a washing component operably coupled to the controller so as to be capable of receiving instructions therefrom and adapted to wash lithium ions or composition having the lithium ions before extraction to remove contaminant;
    a decomposing component operably coupled to the controller so as to be capable of receiving instructions therefrom and adapted to physically decompose the composition having lithium ions;
    a degrading component operably coupled to the controller so as to be capable of receiving instructions therefrom and adapted to chemically degrade the composition having lithium ions;
    a deconstructing component operably coupled to the controller so as to be capable of receiving instructions therefrom and adapted to mechanically deconstruct the composition having lithium ions;
    a sifting component operably coupled to the controller so as to be capable of receiving instructions therefrom and adapted to sift the composition having lithium ions so as to remove material from the lithium ions;
    a waste component operably coupled to the controller so as to be capable of receiving instructions therefrom and adapted to collect waste generated from pre-extraction processing the composition having lithium ions; or a recycle component operably coupled to the controller so as to be capable of receiving instructions therefrom and adapted to collect and recycle materials from the composition having lithium ions.

14. The method of claim 12, further comprising one or more of the following:

a solvent reservoir operably coupled to the controller so as to be capable of receiving instructions therefrom and operably coupled to the complex reactor;

a Li-ion washing component operably coupled to the controller so as to be capable of receiving instructions therefrom and adapted to wash crude lithium ions or the cyclic siloxane-lithium ion complexes;

a pre-extraction filtration component operably coupled to the controller so as to be capable of receiving instructions therefrom and adapted to filter a composition having lithium ions;

a separator component operably coupled to the controller so as to be capable of receiving instructions therefrom and adapted to separate immiscible liquids so as to separate an organic phase having the cyclic siloxane lithium ion complexes from the aqueous phase;

an extract collection component operably coupled to the controller so as to be capable of receiving instructions therefrom and adapted to collect an organic phase extract having the cyclic siloxane-lithium ion complexes;

a drying component operably coupled to the controller so as to be capable of receiving instructions therefrom and adapted to dry the cyclic siloxane-lithium ion complexes so as to remove water therefrom;

a post-extraction filtration component operably coupled to the controller so as to be capable of receiving instructions therefrom and adapted to filter extracted cyclic siloxane-lithium ion complexes;

a lithium salt reactor operably coupled to the controller so as to be capable of receiving instructions therefrom and adapted for forming lithium salts from lithium ions or the cyclic siloxane-lithium ion complexes;

a solvent removal component operably coupled to the controller so as to be capable of receiving instructions therefrom and adapted to remove solvent from lithium ions;

a final wash component operably coupled to the controller so as to be capable of receiving instructions therefrom and adapted to wash the extracted lithium ions;

a purification component operably coupled to the controller so as to be capable of receiving instructions therefrom and adapted to purify the lithium ions;

a lithium ion collection component operably coupled to the controller so as to be capable of receiving instructions therefrom and adapted to collect the lithium ions.

15. The method of claim 1, wherein the processing of the article of manufacture includes one or more of:

removing residual electrical energy from lithium ions in a composition derived from the article of manufacture;

cooling the lithium ions or composition having the lithium ions;

washing lithium ions or composition having the lithium ions before extraction to remove contaminant;

physically decomposing the article of manufacture having the lithium ions;

chemically degrading a composition derived from the article of manufacture having the lithium ions;

mechanically deconstructing the article of manufacture having the lithium ions;

sifting a composition derived from the article of manufacture having lithium ions so as to remove material from the lithium ions;

collecting waste generated from pre-extraction processing of the lithium ions; or collecting and recycling materials from the article of manufacture.

16. The method of claim 1, wherein the processing of the article of manufacture includes removing residual electrical energy from lithium ions in a composition derived from the article of manufacture.

17. The method of claim 1, wherein the processing of the article of manufacture includes cooling the lithium ions or composition having the lithium ions to a temperature less than or about 0° C.

18. The method of claim 1, comprising removing the cyclic siloxane from the lithium ions.

19. The method of claim 1, wherein the article of manufacture includes a battery.

\* \* \* \* \*